US011865026B2

(12) United States Patent
Kusi Boateng

(10) Patent No.: US 11,865,026 B2
(45) Date of Patent: Jan. 9, 2024

(54) MONS PUBIS PUBIC REGION COMPRESSION PAD

(71) Applicant: Victoria Maria Kusi Boateng, Upper Marlboro, MD (US)

(72) Inventor: Victoria Maria Kusi Boateng, Upper Marlboro, MD (US)

( * ) Notice: Subject to any disclaimer, the term of this patent is extended or adjusted under 35 U.S.C. 154(b) by 500 days.

(21) Appl. No.: 16/580,754

(22) Filed: Sep. 24, 2019

(65) Prior Publication Data

US 2020/0093631 A1 Mar. 26, 2020

Related U.S. Application Data

(60) Provisional application No. 62/765,975, filed on Sep. 24, 2018.

(51) Int. Cl.
| | |
|---|---|
| *A61F 5/30* | (2006.01) |
| *A61F 13/66* | (2006.01) |
| *A41C 1/00* | (2006.01) |
| *A61F 13/00* | (2006.01) |
| *A61B 17/00* | (2006.01) |

(52) U.S. Cl.
CPC ............... *A61F 5/30* (2013.01); *A61F 13/66* (2013.01); *A41C 1/003* (2013.01); *A61B 2017/00792* (2013.01); *A61F 2013/0037* (2013.01); *A61H 2205/085* (2013.01)

(58) Field of Classification Search
CPC .... A61F 5/30; A61F 13/66; A61F 2013/0037; A61F 13/472-47272; A61F 13/4702; A41C 1/003; A61B 2017/00792; A61H 2205/085; A61H 1/006; A41B 9/002; A41D 1/088; A41D 13/0525; A63B 71/1216; A63B 71/12

USPC ................................................ 128/96.1, 98.1
See application file for complete search history.

(56) References Cited

U.S. PATENT DOCUMENTS

| | | | | |
|---|---|---|---|---|
| 3,310,053 A | * | 3/1967 | Greenwood | A41C 1/00 450/153 |
| 3,909,847 A | * | 10/1975 | Holt | A41D 1/088 2/466 |
| 4,804,380 A | * | 2/1989 | Lassen | A61F 13/5514 604/385.17 |

(Continued)

OTHER PUBLICATIONS

LipedemaProducts, "Genital Pad Chip Female BiaCare", Dec. 16, 2016 (Year: 2016).*

*Primary Examiner* — Justine R Yu
*Assistant Examiner* — Alexander Morales
(74) *Attorney, Agent, or Firm* — Hoang Steve Ngo

(57) ABSTRACT

A compression pad designed for the Mons pubis area to facilitate a quicker recovery of a patient who has had a tummy tuck or liposuction procedure, which results in a swelling of the Mons pubic region of the body, is disclosed. This compression pad is designed to fit comfortably inside a post operative garment of varying designs to include fajas to compress the skin in this area resulting in a alleviation of swollen tissue, edema, fluid and an esthetic appearance. The compression pad has an elevation of reinforcement areas to relieve the swelling by compression when placed in between a post operative compression garment at the Mons pubis region of the human body. The compression is minimizes the fluid and swelling in the Mons pubis area relieving the patient of the soreness, swelling, and enlargement of the Mons pubis area.

11 Claims, 4 Drawing Sheets

(56) References Cited

U.S. PATENT DOCUMENTS

| | | | | |
|---|---|---|---|---|
| 5,174,307 | A * | 12/1992 | Thompson | A63B 71/1216 |
| | | | | 128/891 |
| 5,483,705 | A * | 1/1996 | DiMatteo | A63B 71/1216 |
| | | | | 2/403 |
| 7,934,507 | B2 * | 5/2011 | Brooks | A41B 9/04 |
| | | | | 2/114 |
| D857,997 | S * | 8/2019 | Bishop | D29/100 |
| 10,575,995 | B2 * | 3/2020 | Hörle | A61F 13/84 |
| 11,344,787 | B2 * | 5/2022 | Vito | A41D 13/05 |
| 2004/0118412 | A1 * | 6/2004 | Piletti-Reyes | A61F 5/30 |
| | | | | 128/876 |
| 2004/0199135 | A1 * | 10/2004 | Engler | A61F 13/471 |
| | | | | 604/386 |
| 2007/0060901 | A1 * | 3/2007 | Alletsee | A61F 13/471 |
| | | | | 604/385.03 |
| 2010/0152687 | A1 * | 6/2010 | Carlozzi | A61F 15/003 |
| | | | | 604/359 |
| 2011/0015708 | A1 * | 1/2011 | Lee | A61F 5/0193 |
| | | | | 128/121.1 |
| 2016/0000153 | A1 * | 1/2016 | Miller | A63B 71/1216 |
| | | | | 128/891 |
| 2018/0008476 | A1 * | 1/2018 | Rodzewicz | A61F 5/30 |
| 2018/0199633 | A1 * | 7/2018 | Henry | A41D 27/28 |

* cited by examiner

MONS PUBIS PUBIC REGION COMPRESSION PAD

CROSS-REFERENCE TO RELATED APPLICATIONS

The present application claims the priority benefit of U.S. Provisional Patent Application Ser. No. 62/765,975, filed on Sep. 24, 2018, which is incorporated herein by reference in its entirety.

BACKGROUND OF THE INVENTION

1. Field of the Invention

This invention comprises a compression pad that is placed inside a post surgical faja garment after liposuction or tummy tuck surgery to apply pressure on the skin in the Mons pubis region of the human body to compress the swollen tissues, edema, and fluid accumulation. From my searching, the Applicant has not seen anyone address this problem in both male or female patients with any personalized designated compression pad designed to fit this area to alleviate the issue of swollen tissue, or fluid retention of the Mons pubis area of the body after surgery.

2. Prior Art

The Applicant could not locate any prior art regarding the Mons pubis area of the human body.

After a treatment of liposuction or a tummy tuck procedure in the human body, wherein it means to remove accumulated fluid or fat by a cannula of suction, swelling arises. It is necessary to compress the specific area of the Mons Pubis pubic area as it can be abnormally enlarged and uncomfortable. It is thereafter necessary to compress this area as to minimize the scar tissue that can develop and the swelling.

It is best to reduce the post operative swelling to reduce scar tissue development and fluid retention in the Mons pubis area resulting in an enlarged Mons pubis. The only thing available on the market are girdles, fajas and pads, but none are designed to put direct pressure on the Mons pubis region. The pads currently used consist of lipo foam used for the flanks and other regions of the body, which are square sheets with rigid edges, the lipo foam is not anatomically cut and designed for exact anatomical pressure to the Mons pubis pubic region as they are flat sheets and are not designed for the pubic region.

In addition, the main complaints from women and men are there is nothing available to adequately compress the swollen and enlargement area of the Mons pubis pubic region, after cosmetic plastic surgery, such as tummy tuck or liposuction. As the lipo foam wrinkles, it has a sticky feel on the human body and does not provide adequate compression in the Mons pubis region.

In light of the above, previous art pads do not apply the adequate pressure conducive for significant shrinkage of the swelling in the Mons pubis skin area of the human body.

SUMMARY OF THE INVENTION

It is a first object to propose a compression pad that anatomically fits the Mons pubis pubic region due to post operative trauma of liposuction or tummy tuck procedures. This pad is made to fit perfectly and comfortably and give adequate compression to minimize swelling.

It is another object of the invention that the pad has a raised surface to provide adequate compression and rounded corners for comfort, without resulting in the development of indented wrinkling of the skin.

Still another object of the invention is to properly alleviate the swelling of the tissues, by applying adequate pressure, and push fluid out toward the lymphatic system of the body to drain properly.

Accordingly, the foregoing objects of this invention are accomplished by the Mons pubis pad described above, specially conformed to the pubic part of the body which has not been addressed before.

Another advantage is the edges are not thick and rough, they are slightly angled and rounded out to fit properly and give compression minimizing additional swelling, alleviating and dissipating existing swelling.

Other advantages of the invention will be provided from the descriptions and accompanying drawings.

DETAILED DESCRIPTION OF THE PREFERRED EMBODIMENTS OF THE INVENTION

Figure 1:
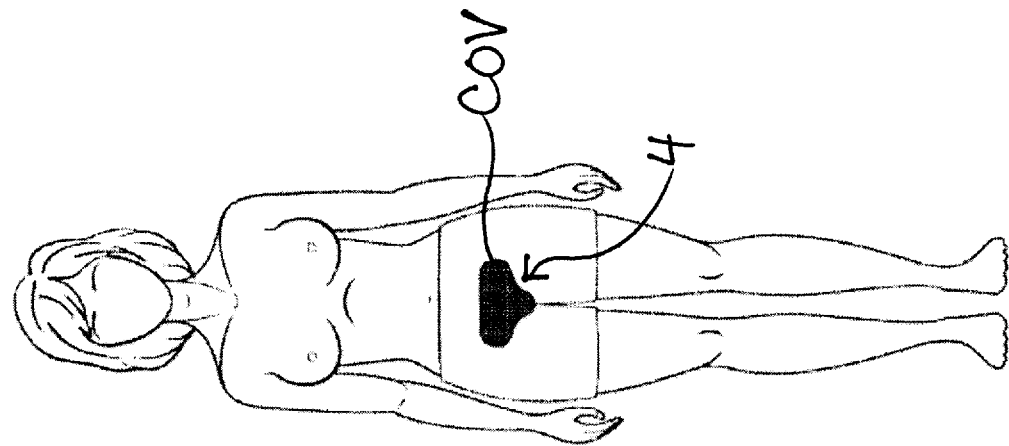
FIG. 1 is an environmental, front view of an embodiment of a compression pad for the Mons pubis pubic region according to the present invention, shown worn by a patient inside a post operative garment or Faja, and wherein a cover is positioned over a reinforcement portion of the compression pad.
Figure 2:
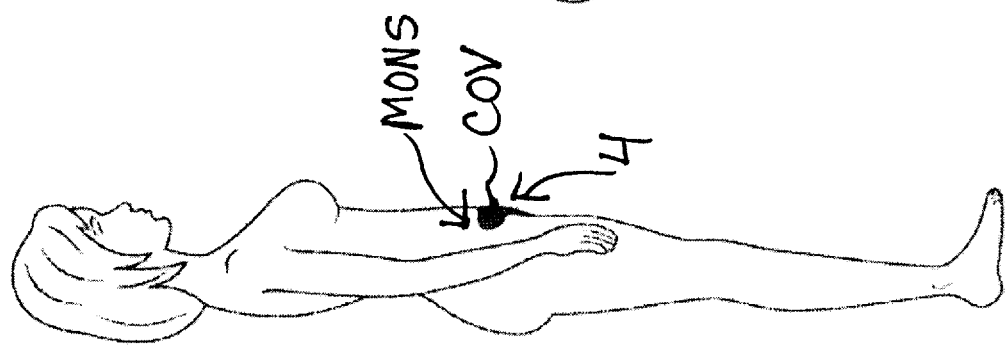
FIG. 2 is an environmental, side view of the compression pad of FIG. 1, designed to be placed on or in front of the Mons pubis region area of a patient, and wherein a cover is positioned over a reinforcement portion of the compression pad.
Figure 3:
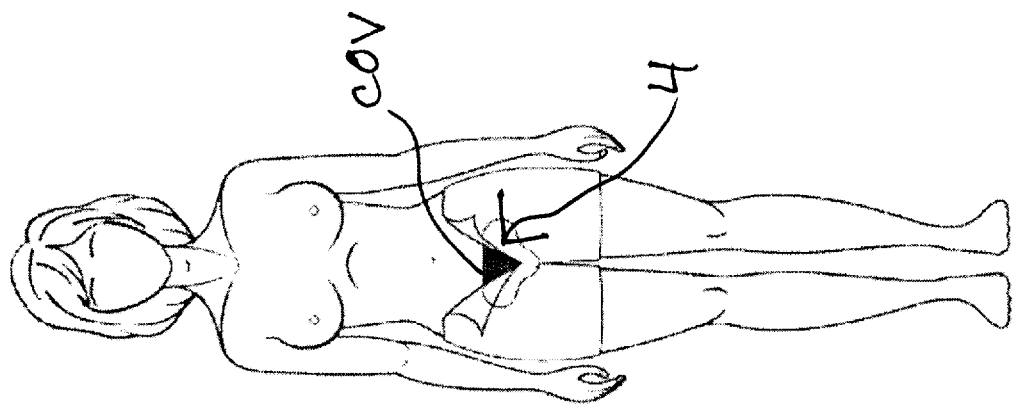
FIG. 3 is an environmental, front view of the compression pad of FIG. 1, positioned inside a compression garment, and wherein a cover is positioned over a reinforcement portion of the compression pad.
Figure 6:
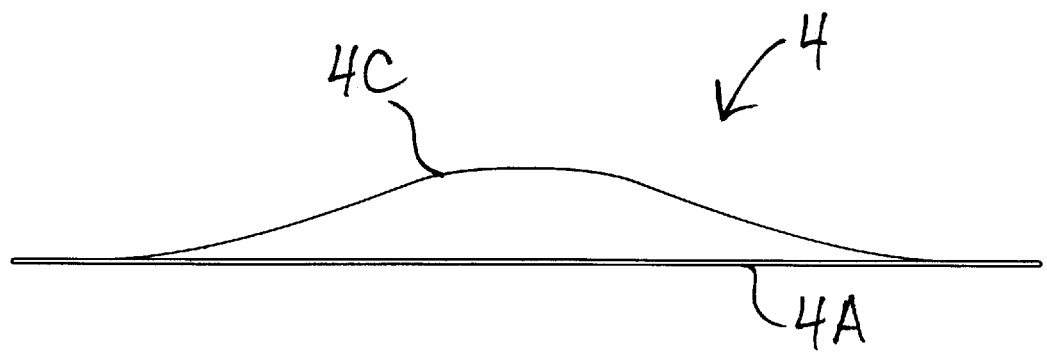
FIG. 6 is a cross sectional view of the compression pad of FIG. 5, from the right side to the left side of the compression pad.
Figure 7:
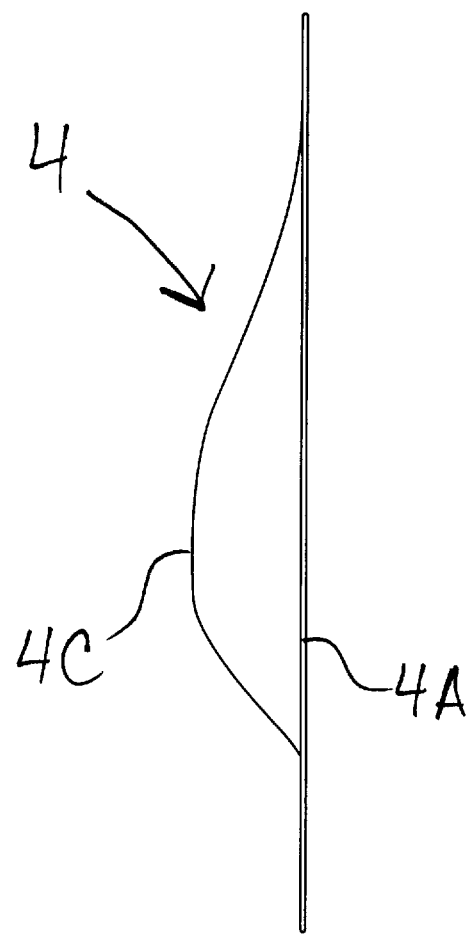
FIG. 7 is a side view of the compression pad of FIG. 5.
Figure 8:
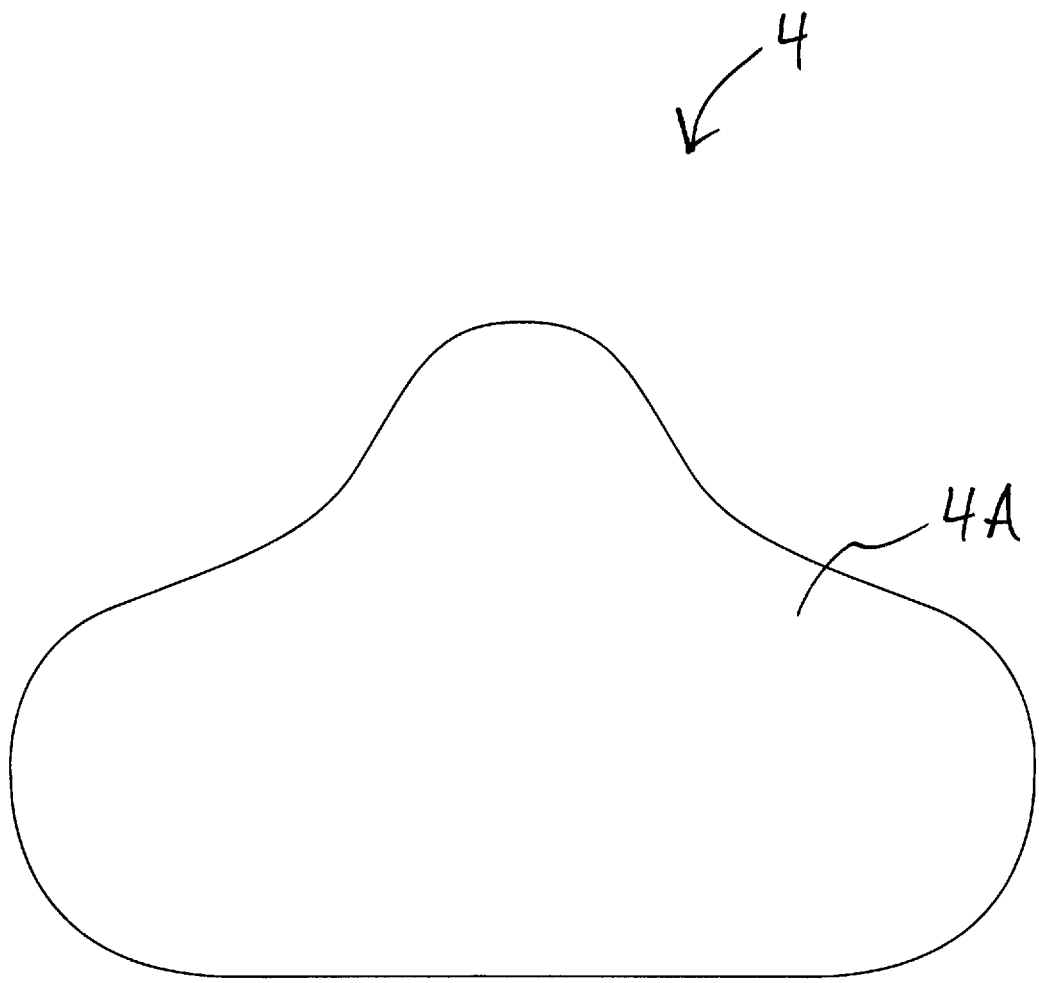
FIG. 8 is a rear view of the compression pad of FIG. 5.

With reference to FIGS. 1-3, a Mons pubis compression pad (4) for the Mons pubis pubic area is depicted therein, which the Mons pubis compression pad (4) worn by a patient after a tummy tuck or liposuction surgery post operative in front of the Mons pubis pubic area MONS. As shown in FIG. 1, the Mons pubis compression pad (4) is being worn by a patient after a tummy tuck procedure inside of a post operative compression garment. The Mons pubis compression pad (4) has a base element (4A) made of plastic, polyurethane, lipo foam material, silicone, or wood surrounded by a cushion material, which may or may not be covered with a soft material cover COV. The Mons pubis compression pad (4) has an elevation rise of material with reinforced areas (4C), the base element (4A), which has a rise gradually starting from the base element (4A) to the highest point of the Mons pubis compression pad (4) of 2.0 cm to 3 cm as shown in FIG. 6, which is a cross sectional view in the middle (4C) for reinforcement, to subside the swelling and elevates to the highest point, of 3 cm and dissipates the outside edge of less than 1 cm. Reinforcement sections (4C) around the base element (4A) starting at the lip portion (4B) of the Mons pubis compression pad (4) (shown in FIG. 4) are positioned to alleviate swelling in the Mons pubis pubic area MONS. The thickness of the reinforcement areas (4C) are 10% to 25% greater than the thickness of the base element (4A). Fluid and swollen tissue is accumulated in the Mons pubis area MONS due to the trauma after the tummy tuck, liposuction or cosmetic surgery effects around the Mons pubis area MONS, interior and inferior, on the back, flanks, or abdominal areas. This process can be avoided by the Mons pubis compression pad (4) when placed inside a post operative compression garment, which will help the swollen skin and fluid dissipate.

As observed in FIG. 1, the Mons pubis compression pad (4) for the Mon pubis pubic area MONS is shaped to surround the Mons pubis pubic area MONS as follows:

From the beginning of the pubic bone externally, the Mons pubis pubic compression pad (4) will extend between 5 and 10 centimeters from this point (A) vertically, to stop above the exterior portion of the external glands, depending on each patient's body shape.

In accordance with the above readings, the regions of the body being encompassed by the Mons pubis compression pad (4) will have a reduction in volume, by the increase of pressure of the Mons pubis compression pad (4) being compressed between the post operative garment and the pubic region, wherein the Mons pubis compression pad (4) is placed. The rise in material on top of the base element (4A) will reinforce the swelling in those portions, which covers the whole Mons pubis region MONS and declines to a flat position at the base with rounded edges for a secure fit and smooth contact with the human body.

Figure 4:
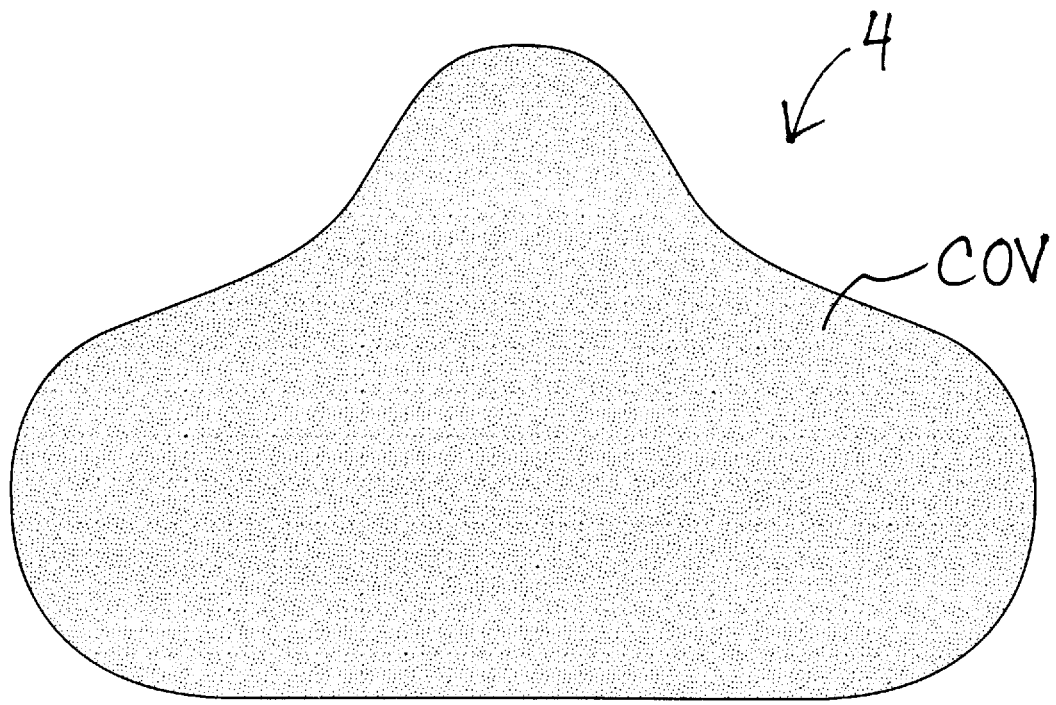
FIG. 4 is a front view of an embodiment of a compression pad for the Mons pubis pubic region according to the present invention, wherein a cover is positioned over a reinforcement portion of the compression pad.
Figure 5:
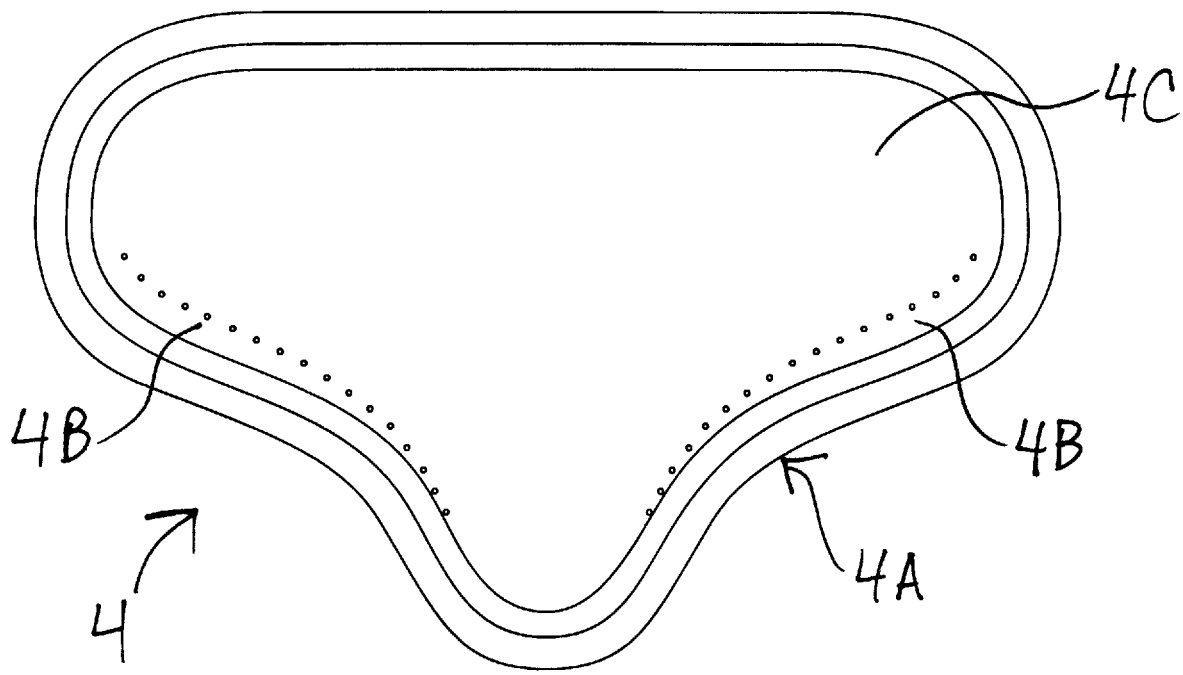
FIG. 5 is a front view of another embodiment of a compression pad for the Mons pubis pubic region according to the present invention, having various alternative dimensions to accommodate different body specifications in the Mons pubis region.

As depicted in FIG. 4, the outer edges, which lie between the left and right iliac regions of the exterior portion of the outer pelvis, the diminish in height ensures swelling dissipation gradually in that area for comfort and esthetic appearance.

The technical characteristics of the Mons pubis compression pad reinforcements (4C) will provide direct pressure wherein there is a rise in foam material, and less pressure toward the outer edges of the Mons pubis compression pad (4).

The invention claimed is:

1. A method of compressing and alleviating swollen tissues, edema, and fluid accumulation of the Mons pubis pubic area of a user, the method comprising:
    positioning a Mons pubis compression pad between an exterior garment being worn by a user and the Mons pubis pubic area of the user,
    wherein said Mons pubis compression pad comprises:
    a base portion comprising a thickness, a perimeter, and a body contained within said perimeter,
    wherein said base portion has a generally upside down triangular configuration defined by an upper left point, an upper right point, a lower central point, and said perimeter,
    wherein said base portion is dimensioned and configured for concentrating compression pressure toward the Mons pubis pubic area of the user during use to compress and alleviate swollen tissues, edema, and fluid accumulation of the Mons pubis pubic areas of the user when said Mons pubis compression pad is positioned in front of pubis pubic area of the user and is being pressured toward the Mons pubis pubic area of the user by of the exterior garment; and
    a reinforcement portion comprising a thickness and a highest point of said reinforcement portion,
    wherein said reinforcement portion continuously tapers downward from said highest point of said reinforcement portion to said perimeter of said base portion, and
    wherein, during use, said reinforcement portion is in closer proximity to the exterior garment as compared to said base portion to the exterior garment while said base portion is in closer proximity to the Mons pubis pubic area of the user as compared to said reinforcement portion to the Mons pubis pubic area of the user.

2. The method of claim 1, wherein said base portion further comprises at least one outside edge having a rounded portion.

3. The method of claim 1, wherein said thickness of said base portion is less than said thickness of said reinforcement portion.

4. The method of claim 1, wherein said Mons pubis compression pad is made in different sizes.

5. The method of claim 1, wherein said Mons pubis compression pad is made of a material selected from the group consisting of silicone, lipo foam, polyurethane, plastic, and wood surrounded by a cushion material.

6. The method of claim 1, further comprising at least one corner being rounded.

7. The method of claim 2, further comprising at least one corner being rounded.

8. The method of claim 1, wherein said thickness of said reinforcement portion is 10% to 25% greater than said thickness of said base portion.

9. The method of claim 1, wherein said Mons pubis compression pad has a total thickness of 2.0 cm to 3 cm.

10. The method of claim 1, wherein said Mons pubis compression pad further comprises at least one outside edge having a rounded portion and at least one corner having a rounded portion.

11. The method of claim 1, wherein said perimeter of said base portion comprises a right perimeter portion, a left perimeter portion, and a top perimeter portion, wherein said right perimeter portion extends from said lower point to said upper right point, wherein said left perimeter portion extends from said lower point to said upper left point, wherein said top perimeter portion extends from said upper right point to said upper left point, and wherein each of said right perimeter portion and said left perimeter portion has a concave configuration.

\* \* \* \* \*